United States Patent
Nakayama et al.

[11] Patent Number: 5,897,315
[45] Date of Patent: Apr. 27, 1999

[54] HANDPIECE HAVING A ROOT CANAL LENGTH MEASUREMENT FUNCTION

[75] Inventors: Shozo Nakayama; Masanobu Yoshida; Hiroaki Kusakabe; Kazunari Matoba, all of Kyoto, Japan

[73] Assignee: Kabushiki Kaisha Morita Seisakusho, Kyoto, Japan

[21] Appl. No.: 08/782,600

[22] Filed: Jan. 13, 1997

[30] Foreign Application Priority Data

Feb. 22, 1996 [JP] Japan .................................... 8-061721

[51] Int. Cl.$^6$ .................................................. A61C 19/04
[52] U.S. Cl. ............................. 433/72; 433/27; 600/590
[58] Field of Search ............................... 433/27, 72, 75, 433/102; 600/589, 590

[56] References Cited

U.S. PATENT DOCUMENTS 4,243,388  1/1981  Arai ........................................ 433/27

FOREIGN PATENT DOCUMENTS

0274169  12/1989  Germany ................................. 433/72
5064643  3/1993  Japan ...................................... 433/102

*Primary Examiner*—Cary E. O'Connor
*Attorney, Agent, or Firm*—Koda & Androlia

[57] ABSTRACT

The present invention discloses a handpiece having a root canal length measurement function, wherein a signal circuit, which is specifically provided for sending measurement signals from a root canal length measurement circuit to a measurement probe mounted on a head provided at the tip of the handpiece, is incorporated in the handpiece, and the signal circuit is electrically connected to the measurement probe via a contact piece in the vicinity of the measurement probe. Therefore, it is not necessary to connect the signal circuit for measurement by way of the outside of the handpiece. In addition, this structure improves the operability of the handpiece because there is no lead wire for connection. Furthermore, this structure eliminates the troublesome task of externally connecting lead wires to the head of the handpiece, which would otherwise be required at each treatment time. Moreover, the signal circuit is securely formed without passing through a drive power transmission mechanism, thereby preventing unstable operation of root canal length measurement due to instantaneous opening of the signal circuit. Additionally, it is possible to use a cutting tool having a shank portion and a cutting portion insulated from each other.

14 Claims, 7 Drawing Sheets

HANDPIECE HAVING A ROOT CANAL LENGTH MEASUREMENT FUNCTION

BACKGROUND OF THE INVENTION

1. Field of the Invention

The present invention relates to improvements in a handpiece having a root canal length measurement function for a dental treatment apparatus.

2. Description of the Prior Art

An apparatus capable of conducting root canal treatment while performing root canal measurement by using a cutting tool, such as a file or a reamer, which is also used as a measurement probe, is known. In this case, since the cutting tool is used as one of the electrodes of a root canal length measurement circuit, measurement signals are required to be sent to the cutting tool via lead wires. Such lead wires are conventionally connected by way of the outside of the handpiece of an apparatus. This causes the problem of impairing the operability of the handpiece because of nuisance due to the existence of the lead wires, and also causes the problem of requiring the troublesome task of externally connecting the lead wires to the head of the handpiece at each treatment time.

In order to solve these problems, the inventors of the present application paid attention to the fact that the drive power transmission mechanism in the handpiece comprises metallic members, namely electrically conductive members, and have proposed that a tool holding mechanism should be connected to the root canal length measurement circuit by using the drive power transmission mechanism as a signal circuit (refer to Japanese Laid-open Patent Application 7-328034, for example). However, in this proposal, the signal circuit may be opened instantaneously as gears are rotated, raising the possibility of unstable measurement operation. Furthermore, in a type of cutting tool, the cutting tool's shank portion installed in the measurement probe holding mechanism of the handpiece and the cutting portion at the tip of the cutting tool are insulated from each other. This type of cutting tool cannot be used for the handpiece proposed above.

SUMMARY OF THE INVENTION

Accordingly, a first object of the present invention is to eliminate the need for external connection of lead wires for a root canal length measurement circuit. A second object of the present invention is to improve the operability of a handpiece. A third object of the present invention is to attain stable root canal length measurement.

In order to attain the above-mentioned objects, the handpiece having a root canal length measurement function in accordance with the present invention comprises a signal circuit, which is specifically provided for sending measurement signals from a root canal length measurement circuit to a measurement probe mounted on a head provided at the tip of the handpiece, being incorporated in the handpiece, and a contact piece electrically connected to the signal circuit, wherein the signal circuit is electrically connected to the measurement probe in the vicinity of the measurement probe via the contact piece. With this structure, it is not necessary to connect the signal circuit for measurement by way of the outside of the handpiece. In addition, this structure improves the operability of the handpiece because there is no lead wire for connection. Furthermore, this structure eliminates the troublesome task of externally connecting lead wires to the head of the handpiece, which would otherwise be required at each treatment time. Moreover, the signal circuit is securely formed without passing through a drive power transmission mechanism, thereby preventing unstable operation of root canal length measurement due to instantaneous opening of the signal circuit. Additionally, it is possible to use a cutting tool having a shank portion and a cutting portion insulated from each other.

The above-mentioned root canal length measurement circuit can be incorporated into the handpiece or installed in a separate control unit. In the latter case, the signal circuit is connected to the root canal length measurement circuit via a tube for connecting the handpiece to the control unit.

Furthermore, the above-mentioned contact piece is provided on the lower surface of the head and supported so as to be rotatable vertically in the axial direction of the measurement probe, and the contact piece holds the measurement probe between the tip portions thereof when rotated upward, thereby establishing electrical connection. With this structure, the measurement probe can be mounted and dismounted easily. In particular, in case the measurement probe is dismounted, when the measurement probe is released and extracted downward, the holding operation by the contact piece is automatically released, whereby the dismounting operation can be conducted easily. Other structures can also be used: a structure wherein the contact piece is provided on the lower surface of the head and supported so as to be rotatable across the measurement probe, and the contact piece is electrically connected to the measurement probe when rotated in the direction that makes contact with the measurement probe; and another structure wherein the contact piece is provided on the lower surface of the head and supported so as to be movable in the axial direction of the handpiece, and the contact piece is electrically connected to the measurement probe when projected in the direction that makes contact with the measurement probe.

Since the housing of the head is made of an insulating material, metallic members exposed on the upper surface of the head are electrically insulated from the measurement probe held in the head. With this structure, measurement is not adversely affected even when the cap assembly of the measurement probe holding mechanism of the handpiece makes contact with tissues inside the mouth of a patient during dental operation, whereby the operability of the handpiece can be improved, and stable root canal length measurement can be attained. This insulation structure can be attained, for example, when the handpiece has a structure wherein an integrally secured metallic support ring is provided at the upper portion of the housing of the head, and the cap assembly of the measurement probe holding mechanism is mounted by screw engagement of the support ring.

Figure 2:
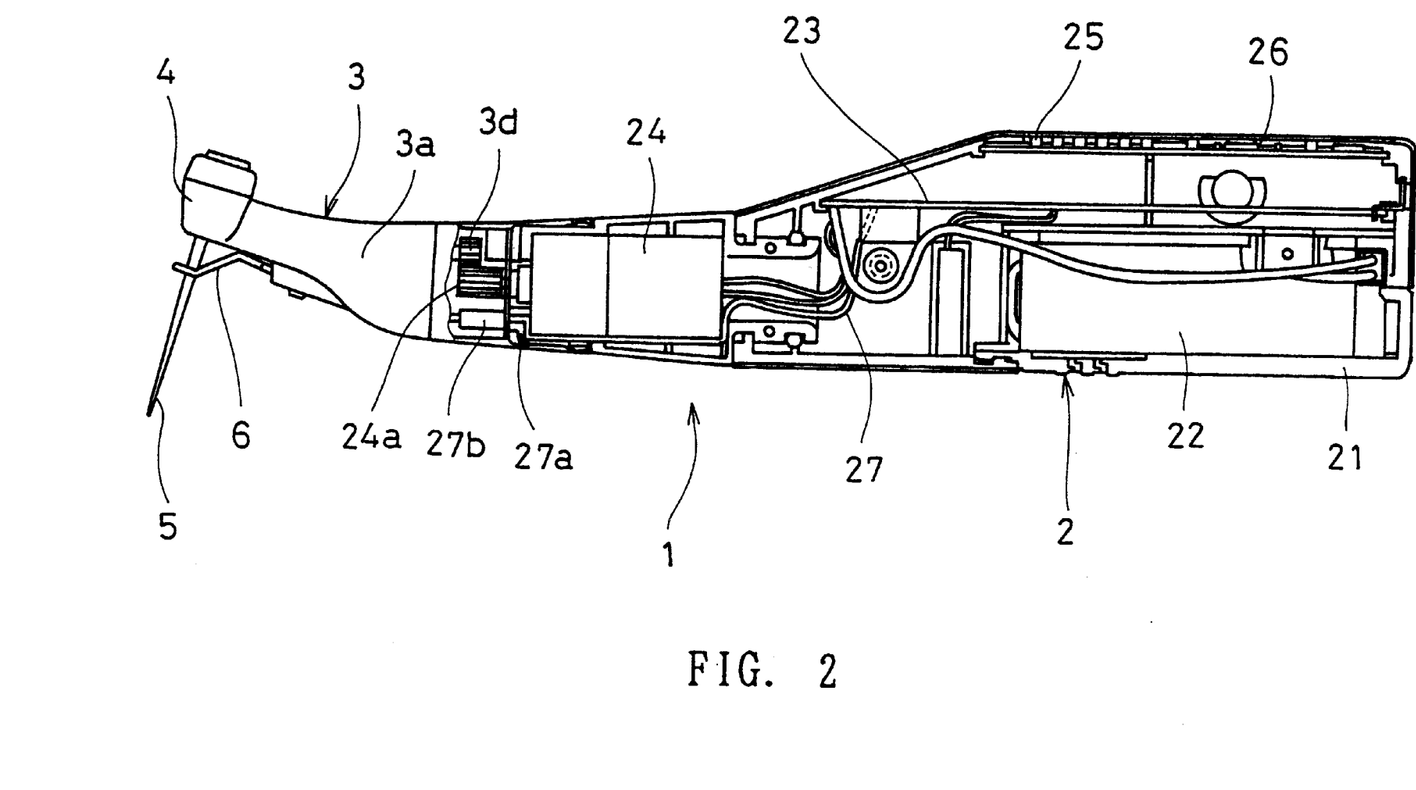
FIG. 2 is a partially sectional side view showing the entire handpiece.

Words "upper", "lower" and the like in this specification are based on the posture of the handpiece shown in FIG. 2.

Specific structures of the handpiece in accordance with the present invention will be clarified by referring to explanations regarding the following embodiments.

DETAILED DESCRIPTION OF THE PREFERRED EMBODIMENTS

An embodiment of the present invention is described below. This embodiment relates to a cordless handpiece containing a motor, a power supply battery, a root canal length measurement circuit, etc. in the main unit of the handpiece. However, the present invention is not limited to such a cordless type but is applicable to a type of handpiece which supplies motor drive power or the like from a separate control unit via a tube. In this case, the root canal length measurement circuit can also be installed in the separate control unit, and a signal circuit is connected to the root canal length measurement circuit via a tube.

Referring to the figures, numeral 1 represents a handpiece comprising a main handpiece unit 2 and a head unit 3. The head unit 3 is installed at the tip of the main handpiece unit 2. The case 21 of the main handpiece unit 2 contains a battery 22, a printed circuit board 23, a motor 24, etc. The upper portion of the case 21 is provided with a display portion 25 and an operation portion 26 equipped with a plurality of switches. The printed circuit board 23 contains a control circuit for controlling the entire operation of the handpiece, a root canal length measurement circuit, etc. Components and the like mounted on the printed circuit board 23 are not shown.

Numeral 27 represents a lead wire connected to one of the output terminals of the above-mentioned root canal length measurement circuit, and the tip portion of the lead wire 27 is connected to a terminal jack 27b provided on a terminal plate 27a rotatably installed at the tip portion of the main handpiece unit 2. Furthermore, the motor 24 is disposed at the tip portion of the main handpiece unit 2, and the output gear 24a of the motor 24 projects forward.

The head unit 3 comprises a head 4 integrated at the tip of the shank portion 3a thereof. The base of the shank portion 3a is provided with a cylindrical portion 3b. By inserting the tip of the main handpiece unit 2 into the cylindrical portion 3b, the head unit 3 is connected to the main handpiece unit 2 so as to be rotatable around the main handpiece unit 2 within a certain range. Numeral 4a represents a tool holding mechanism provided in the head 4, and numeral 3c represents a plastic housing formed so as to integrate portions ranging from a portion surrounding the head 4 to the shank portion 3a. An intermediate gear 3d and a terminal pin 3e connected to the terminal jack 27b are provided at the bottom of the cylindrical portion 3b. The head side portion of the terminal pin 3e is formed as a contact plug 3f.

Since the head unit 3 is rotatable around the main handpiece unit 2 within a certain range as described above, a cutting tool 5 can be directed in a predetermined direction by rotating the head unit 3 while the display portion 25 and the operation portion 26 remain directed in a direction convenient for the operator. The lead wire 27 has a length sufficient for the rotation range.

An intermediate shaft 3g is provided in the shank portion 3a of the head unit 3. When the head unit 3 is mounted on the main handpiece unit 2, the terminal pin 3e is connected to the terminal jack 27b, and the intermediate gear 3d engages the output gear 24a of the motor 24. As a result, the rotation of the motor 24 is transmitted to a rotor shaft 4c via a rear gear 3h and a front gear 3j on the intermediate shaft 3g and a rotor gear 4b in the tool holding mechanism 4a of the head 4.

Figure 3:
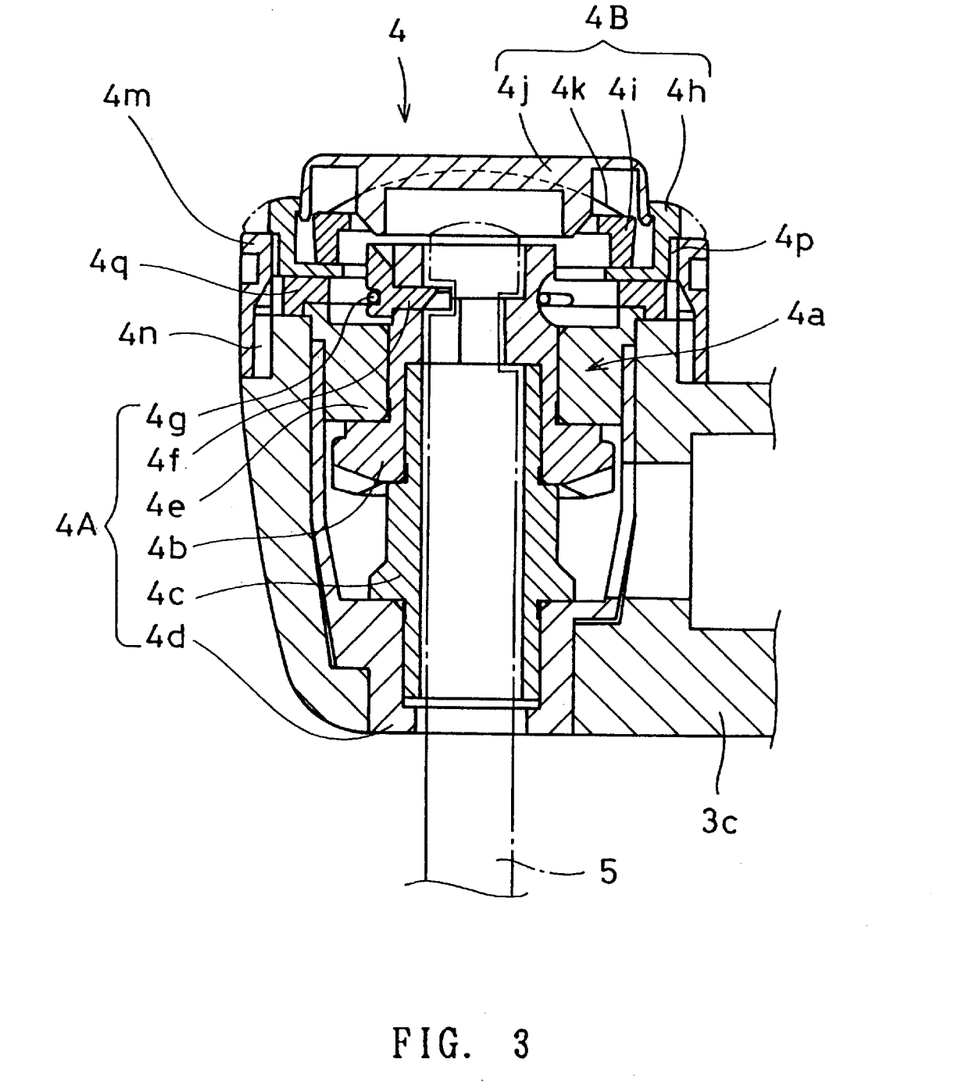
FIG. 3 is a sectional view showing the head of the handpiece.

As shown in FIG. 3, the tool holding mechanism 4a comprises a rotor assembly 4A and a cap assembly 4B. The rotor assembly 4A comprises a head collar 4d, a bearing 4e, a rotor gear 4b, a rotor shaft 4c, a chuck pawl 4f and a C-ring 4g. In addition, the cap assembly 4B comprises a cap ring 4h, a spacer 4i, a push cap 4j and a cap spring 4k. These structures are basically identical to conventional structures.

Numeral 5 represents a cutting tool, such as a file, which is also used as a measurement probe at the time of root canal measurement. The cutting tool 5 is mounted on the head 4 by the tool holding mechanism 4a.

Figure 1:
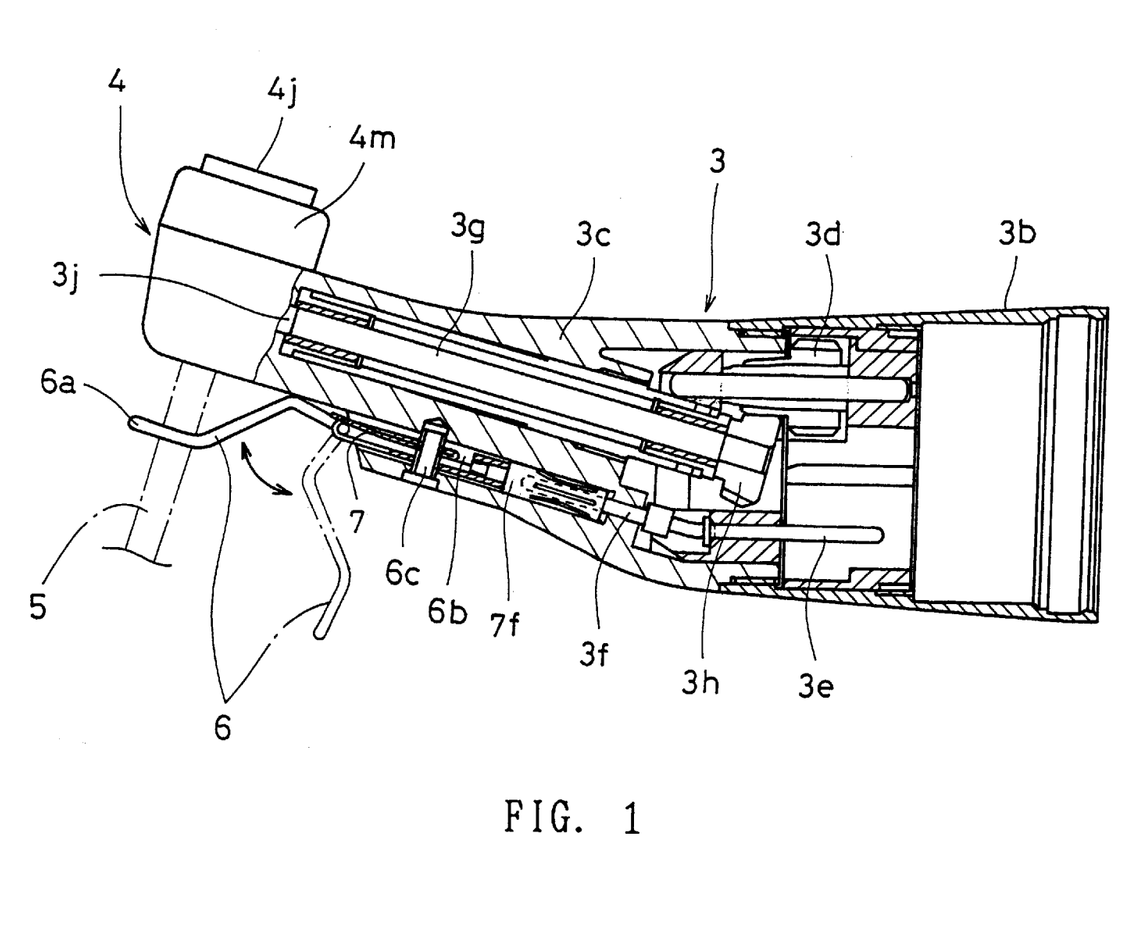
FIG. 1 is a partially sectional side view showing the head unit of a handpiece in accordance with an embodiment of the present invention.
Figure 4:
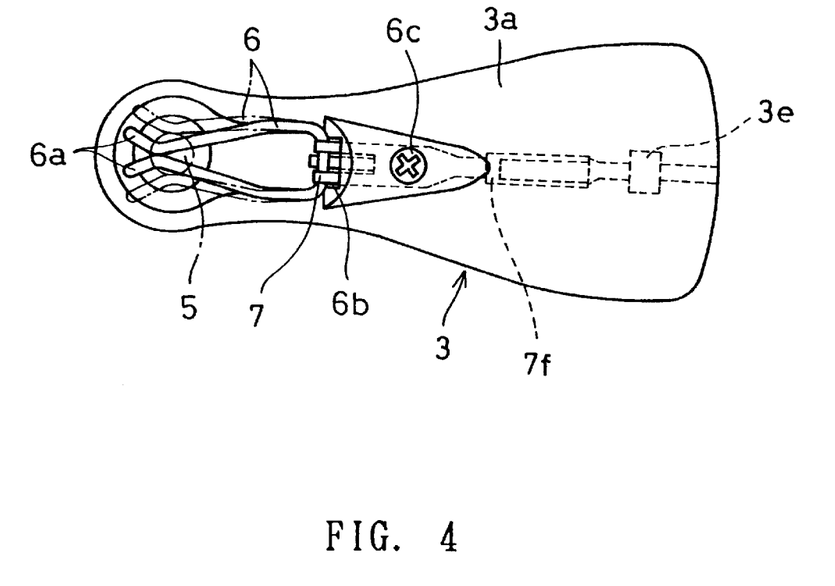
FIG. 4 is a bottom view showing an embodiment of the tip portion of the head unit of the handpiece.
Figure 5A:
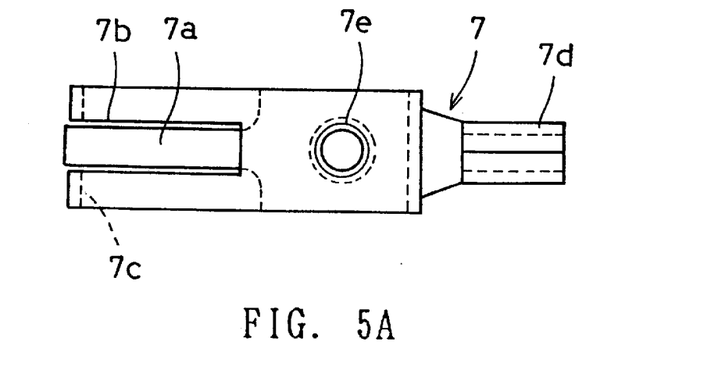
FIG. 5A is a plan view showing a contact plate disposed at the head unit.
Figure 5B:
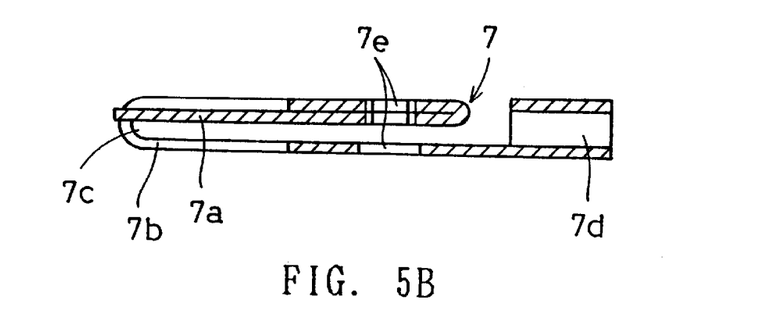
FIG. 5B is a sectional view showing the contact plate.
Figure 5C:
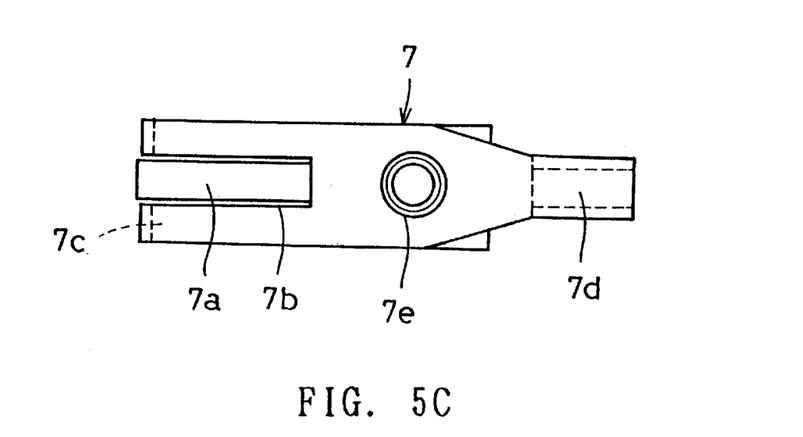
FIG. 5C is a bottom view showing the contact plate.
Figure 6A:
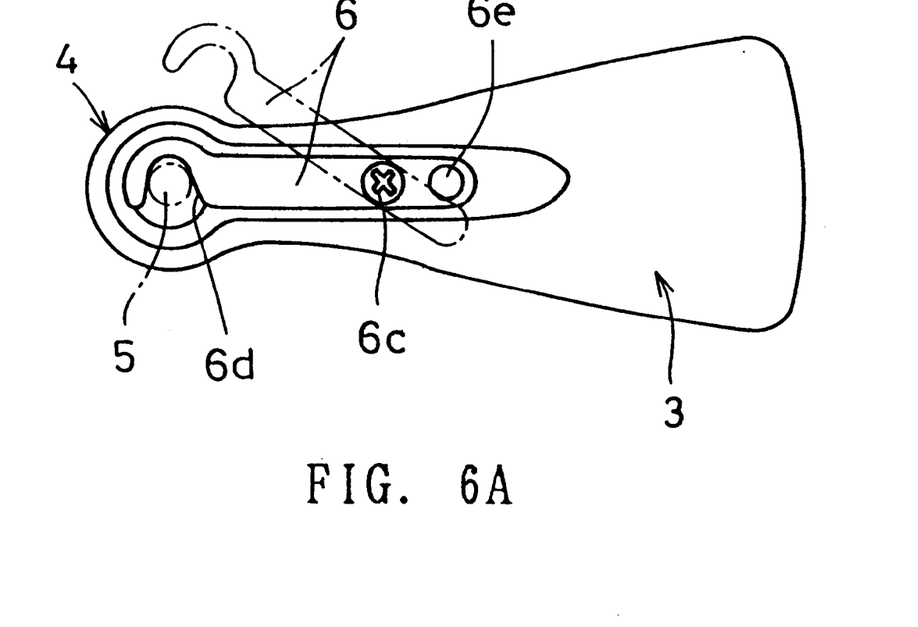
FIG. 6A is a bottom view showing another embodiment of the tip portion of the head unit.
Figure 6B:
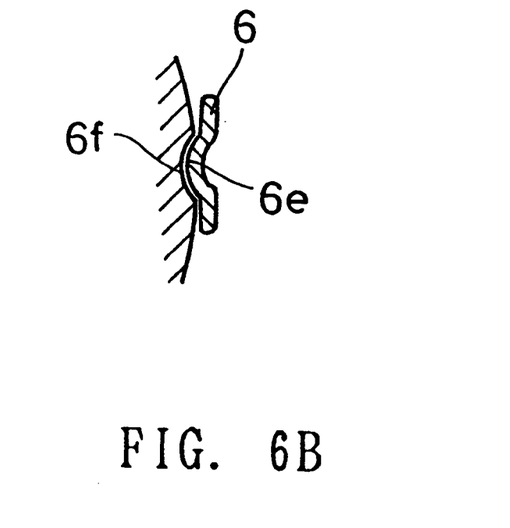
FIG. 6B is a sectional view showing the main section of the tip portion.

Numeral 6 represents a contact piece. As shown in FIGS. 1 and 4, an elastic metal wire is bent into a U-shape which is bilaterally symmetrical, the two wire portions of the U-shaped wire are bent inward at their intermediate positions so as to make contact with each other, and further bent downward, and then the tips of the two wire portions are bent outward so as to form a guide portion 6a. Numeral 7 represents an elastic narrow contact plate made of metal. As shown in FIGS. 5A, 5B and 5C, a narrow tongue piece 7a is formed along the center line of one end portion of the contact plate 7 and then folded back. At the position corresponding to the tongue piece 7a, a portion having a slit 7b along the center line is folded back so as to form a U-shape, thereby forming a contact piece holding portion 7c. At the other end portion of the contact plate 7, a cylindrical curl portion 7d is formed, and two holes 7e passing through in the vertical direction are also formed; one of the holes 7e is internally threaded. A contact jack 7f is crimped onto the curl portion 7d.

The contact piece 6 having the above-mentioned structure can be attached to the contact plate 7 by fitting the central portion of the contact piece 6 into the contact piece holding portion 7c of the contact plate 7 and by pressing the contact piece 6 with the tongue piece 7a. Furthermore, by inserting the contact plate 7 into a contact piece mounting hole 6b formed in the lower surface of the shank portion 3a, the contact plate 7 is mounted on the head unit 3, and the contact jack 7f is connected to the contact plug 3f. Since the contact piece 6 is held with the tongue piece 7a, the contact piece 6 securely makes contact with the contact plate 7, thereby preventing improper contact. Numeral 6c represents a set screw for preventing the contact plate 7 from slipping off. With this set screw 6c removed, the contact piece 6 can be mounted on or dismounted from the head unit 3 together with the contact plate 7, whereby the contact piece 6 and the contact plate 7 can be sterilized or replaced without hindrance.

In the condition wherein the contact piece 6 is mounted on the head unit 3, the contact piece 6 is rotatable around the contact piece holding portion 7c in the vertical direction indicated by the arrows shown in FIG. 1, that is, in the axial direction of the cutting tool 5. The cutting tool 5 is mounted on the head 4 while the contact piece 6 is rotated downward as indicated by the chain line shown in FIG. 1, and then the contact piece 6 is rotated upward. When the contact piece 6 is rotated upward, the cutting tool 5 is inserted into the guide portion 6a and held between the tip portions thereof as indicated by the chain line shown in FIG. 4. In this condition, a continuous circuit is formed in the range from the lead wire 27 to the contact piece 6 via the terminal jack 27b, the terminal pin 3e, the contact plug 3f, the contact jack 7f and the contact plate 7.

This circuit is a signal circuit specifically provided for root canal length measurement. With this circuit, the cutting tool 5 is electrically connected to the root canal measurement circuit provided on the printed circuit board 23 of the main handpiece unit 2. In the above-mentioned embodiment, the lead wire 27 used as a part of the signal circuit passes through the internal space of the main handpiece unit 2. However, this structure is taken just as an example. Instead of this structure, other structures can also be adopted as necessary. For example, a signal circuit can be formed by way of a conductor integrally incorporated in the case 21 or disposed along the case 21.

When rotated toward the tip of the cutting tool 5, the contact piece 6 is moved away from the cutting tool 5, and the cutting tool 5 having been held is released. In this condition, the cutting tool 5 can be dismounted from the tool holding mechanism 4a. However, even in the condition wherein the cutting tool 5 is held with the contact piece 6, when the cutting tool 5 is dismounted from the tool holding mechanism 4a and extracted downward, the contact piece 6 is rotated downward as the cutting tool 5 is moved, thereby automatically releasing the cutting tool 5. Consequently, the cutting tool 5 can be dismounted even when the contact piece 6 has not been rotated downward in advance.

The other output terminal (not shown) of the root canal measurement circuit is connected to a grounding electrode via a lead wire connected to a terminal provided at the trailing end of the main handpiece unit 2, for example.

The plastic housing 3c of the head unit 3 is molded by using PPS resin, PBT resin, ABS resin or the like. By electrically insulating metallic parts exposed in the upper portion of the tool holding mechanism 4a from the cutting tool 5, measurement is not adversely affected even when portions other than the cutting tool 5 and the contact 6 make contact with tissues inside the mouth of a patient during dental operation, whereby the operation can be conducted easily. Instead of synthetic resin, other insulation materials, such as ceramics, can also be used when molding the housing 3c.

However, a general type of conventional tool holding mechanism is structured so that after the rotor assembly is incorporated into the head housing, the cap ring of the cap assembly is directly screwed into the housing to secure the cap assembly. Therefore, in case the housing 3c is made of synthetic resin just as in the case of the present invention, and when mounting/dismounting operations are repeated or sterilization is repeated at such a high temperature as that generated in an autoclave, the threaded portion on the housing side is slightly deformed, and the connection becomes loose. For this reason, the structure wherein the cap ring is directly screwed into the housing cannot be adopted. A pressure-fit structure cannot be adopted either, since loose connection also occurs in the case of the pressure-fit type.

To solve the problem, this embodiment of the present invention establishes the above-mentioned insulation by changing a part of the known structure of the conventional tool holding mechanism as shown in FIG. 3. In other words, a metallic support ring 4m is secured to the upper end of the portion covering the periphery of the tool holding mechanism 4a of the housing 3c. The upper portion of the support ring 4m is threaded, and the cap ring 4h is screwed into the threaded upper portion. The support ring 4m is secured to the housing 3c, for example, by using both screw tightening and adhesion, that is, by forming threads on both mating members, by applying adhesive to the members and by engaging the members with each other. Numeral 4n represents a securing portion attained by the above-mentioned means. This securing can also be obtained by using other means, such as insertion molding wherein embedding is performed while the housing is molded so as to attain integral molding.

Furthermore, numeral 4p represents a screw-engagement portion between the support ring 4m and the cap ring 4h. The cap assembly 4B is mounted and dismounted by using this screw-engagement portion 4p. The rotor assembly 4A is inserted into or taken out of the housing 3c while the cap assembly 4B is dismounted. Therefore, the overhaul and sterilization of the tool holding mechanism 4a can be performed without hindrance. Moreover, since the screw-engagement portion 4p is a metal-to-metal contact portion, sufficient durability can be obtained to withstand repeated mounting/dismounting operations and high-temperature treatment, whereby secure installation can be attained.

Since the cap ring 4h is screwed into the support ring 4m secured to the plastic housing 3c as described above, the cap assembly 4B is insulated from the rotor assembly 4A. Therefore, even when the cutting tool 5 mounted in the rotor assembly 4A is connected to the root canal length measurement circuit via the components of the signal circuit, such as the contact piece 6 and the like, the cap assembly 4B is kept insulated from these components of the signal circuit, thereby ensuring stable root canal measurement. Numeral 4q represents an insulation ring inserted between the rotor assembly 4A and the cap assembly 4B so as to ensure the insulation condition. The insulation ring 4q prevents electrical contact between the bearing 4e and the cap ring 4h.

Structures other than those mentioned above can also be adopted as a structure for electrically connecting the signal circuit for root canal measurement to the cutting tool 5 via the contact piece 6. FIGS. 6A, 6B, 7A and 7B show embodiments of the other structures. The embodiment shown in FIGS. 6A and 6B corresponds to claim 5. A narrow plate-like contact piece 6 is mounted on the lower surface of the housing 3c so as to be rotatable across the cutting tool 5. A cutout portion 6d formed in the side fringe of the tip of the contact piece 6 is engaged with the cutting tool 5 so as to establish electrical connection. The connection to the internal signal circuit is attained as necessary by way of the set screw 6c. The position of a convex portion 6e formed on the contact piece 6 corresponds to that of a concave portion 6f formed in the housing 3c. When the cutout portion 6d is engaged with the cutting tool 5, the convex portion 6e accurately fits into the concave portion 6f so as to securely maintain connection between the contact piece 6 and the cutting tool 5.

Figure 7A:
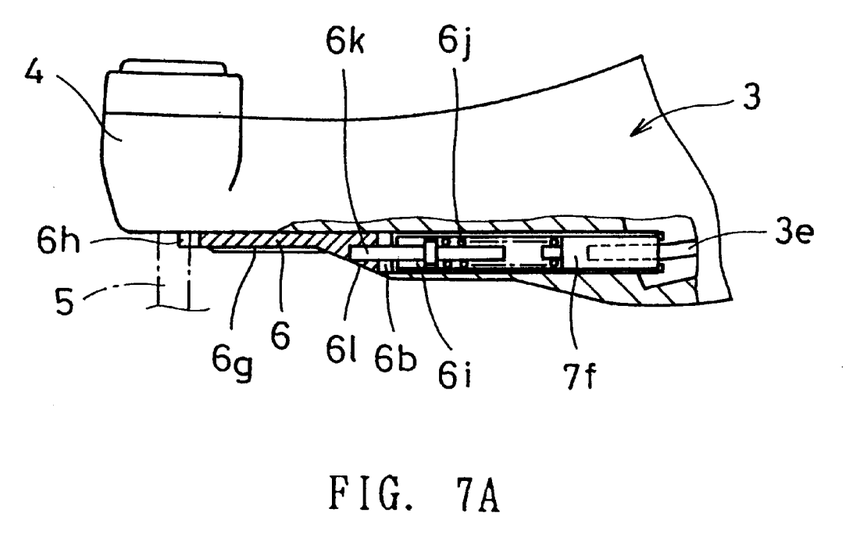
FIG. 7A is a partially sectional side view showing still another embodiment of the tip portion of the head unit.
Figure 7B:
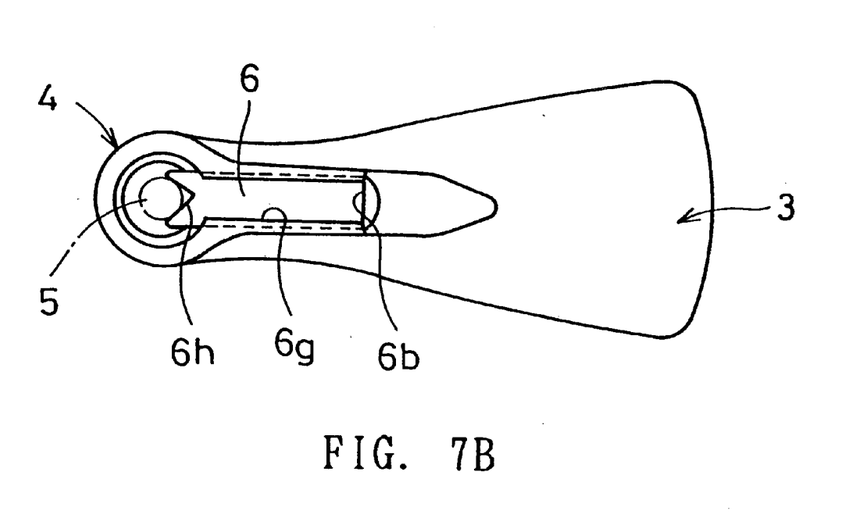
FIG. 7B is a bottom view showing the tip portion.

The embodiment shown in FIGS. 7A and 7B corresponds to claim 6. A plate-like contact piece 6 is supported by a guide portion 6g formed on the lower surface of the housing 3c so as to be slidable in the left-to-right direction in the figures. A V-shaped cutout portion 6h formed at the tip of the contact piece 6 is pushed against the cutting tool 5 so as to establish electrical connection. Numeral 6i represents a contact piece connector. By inserting the contact piece connector 6i into the contact piece insertion hole 6b, just as the above-mentioned contact plate 7 is inserted, a circuit is formed between the internal signal circuit and the contact piece 6. In addition, the contact piece 6 is pushed against the cutting tool 5 by a push pin 6k energized by a compression spring 6j so as to securely maintain the connection condition. The mounting and dismounting operations of the cutting tool 5 can be performed after the inclined portion 6l is pushed so as to move the contact piece 6 to the right.

What is claimed is:

1. A handpiece having a root canal length measurement function, comprising:

a signal circuit for sending measurement signals from a root canal length measurement circuit to a measurement probe mounted on a head provided at the tip of said handpiece, said signal circuit incorporated into and provided inside of said handpiece, and a contact piece incorporated into and provided within said handpiece and electrically connected to said signal circuit, wherein said signal circuit is electrically connected to said measurement probe in the vicinity of said measurement probe via said contact piece.

2. A handpiece having a root canal length measurement function according to claim 1, wherein said root canal length measurement circuit is incorporated in said handpiece.

3. A handpiece having a root canal length measurement function according to claim 1, wherein said signal circuit is connected to a root canal length measurement circuit provided in a separate control unit via a tube for connecting said handpiece to said separate control unit.

4. A handpiece having a root canal length measurement function according to claim 1, 2 or 3, wherein said contact piece is provided on the lower surface of said head and supported so as to be rotatable vertically in the axial direction of said measurement probe, and said contact piece is electrically connected to said measurement probe by holding said measurement probe between the tip portions thereof when rotated in the upward direction that makes contact with said measurement probe.

5. A handpiece having a root canal length measurement function according to claim 1, 2 or 3, wherein said contact piece is provided on the lower surface of said head and supported so as to be rotatable across said measurement probe, and said contact piece is electrically connected to said measurement probe when rotated in the direction that makes contact with said measurement probe.

6. A handpiece having a root canal length measurement function according to claim 1, 2 or 3, wherein said contact piece is provided on the lower surface of said head and supported so as to be movable in the axial direction of said handpiece, and said contact piece is electrically connected to said measurement probe when projected in the direction that makes contact with said measurement probe.

7. A handpiece having a root canal length measurement function according to claim 1, 2 or 3, wherein the housing of said head is made of an insulating material, and metallic members exposed on the upper surface of said head is electrically insulated from said measurement probe held in said head.

8. A handpiece having a root canal length measurement function according to claim 4, wherein the housing of said head is made of an insulating material, and metallic members exposed on the upper surface of said head is electrically insulated from said measurement probe held in said head.

9. A handpiece having a root canal length measurement function according to claim 5, wherein the housing of said head is made of an insulating material, and metallic members exposed on the upper surface of said head is electrically insulated from said measurement probe held in said head.

10. A handpiece having a root canal length measurement function according to claim 6, wherein the housing of said head is made of an insulating material, and metallic members exposed on the upper surface of said head is electrically insulated from said measurement probe held in said head.

11. A handpiece having a root canal length measurement function according to claim 7, wherein an integrally secured metallic support ring is provided at the upper portion of said housing of said head, and the cap assembly of a measurement probe holding mechanism is mounted by screw engagement of said support ring.

12. A handpiece having a root canal length measurement function according to claim 8, wherein an integrally secured metallic support ring is provided at the upper portion of said housing of said head, and the cap assembly of a measurement probe holding mechanism is mounted by screw engagement of said support ring.

13. A handpiece having a root canal length measurement function according to claim 9, wherein an integrally secured metallic support ring is provided at the upper portion of said housing of said head, and the cap assembly of a measurement probe holding mechanism is mounted by screw engagement of said support ring.

14. A handpiece having a root canal length measurement function according to claim 10, wherein an integrally secured metallic support ring is provided at the upper portion of said housing of said head, and the cap assembly of a measurement probe holding mechanism is mounted by screw engagement of said support ring.

* * * * *